United States Patent [19]

Aouda et al.

[11] Patent Number: 4,919,919

[45] Date of Patent: Apr. 24, 1990

[54] NITROGLYCERIN SPRAY

[75] Inventors: Yukio Aouda, Tokyo; Hiroshi Ninomiya, Sayama; Genichi Izu, Saitama; Yuichi Yazawa; Megumi Tachibana, both of Tokyo, all of Japan

[73] Assignee: Nippon Kayaku Kabushiki Kaisha, Tokyo, Japan

[21] Appl. No.: 244,487

[22] Filed: Sep. 14, 1988

[30] Foreign Application Priority Data

Sep. 30, 1987 [JP] Japan ................. 62-244259

[51] Int. Cl.$^5$ .......................... A61K 9/08; A61K 9/12; A61K 9/72; A61K 31/21
[52] U.S. Cl. ......................................... 424/45; 514/509
[58] Field of Search ............................ 424/45; 514/509

[56] References Cited

U.S. PATENT DOCUMENTS

| | | | |
|---|---|---|---|
| 2,868,691 | 1/1959 | Purush et al. | 424/45 |
| 3,050,443 | 8/1962 | Kraus | 424/45 |
| 3,106,511 | 10/1963 | Cuttler et al. | 424/45 |
| 3,155,574 | 11/1964 | Silson et al. | 424/343 |
| 4,112,115 | 9/1978 | Coghlan | 514/509 |
| 4,323,577 | 4/1982 | Ohkuma et al. | 514/509 |
| 4,615,699 | 10/1986 | Gale et al. | 604/897 |

FOREIGN PATENT DOCUMENTS

| | | | |
|---|---|---|---|
| 0116944 | 8/1984 | European Pat. Off. | 514/509 |
| WO82/03172 | 9/1982 | PCT Int'l Appl. | 514/509 |
| 970027 | 9/1964 | United Kingdom . | |

OTHER PUBLICATIONS

Teo et al., C.A. 107 #64738g, 1985, (pub. 1987).
Shcherbakova, C.A. 94 #76910h, (1981).
Contractor, C.A. 81 #82331t, (1974).
Contractor, C.A. 76 #63153s, (1972).

Primary Examiner—Shep K. Rose
Attorney, Agent, or Firm—Henry C. Nields

[57] ABSTRACT

The present invention relates to a nitroglycerin spray prepared by filling a solution comprising nitroglycerin, ethanol and water and having a pH of about 2.4 to about 6.7 into a liquid-pressurized container.

2 Claims, No Drawings

NITROGLYCERIN SPRAY

BACKGROUND OF THE INVENTION

Known nitroglycerin sprays include, for example, one prepared by filling a composition comprising nitroglycerin, propanediol, dehydrated ethanol and a propellant such as dichlorodifluoromethane (hereinafter referred to as a "flon gas") into a gas-pressurized container (see Japanese Patent Publication No. 10718/1966) and one prepared by filling a composition comprising nitroglycerin, a capric/caproic acid glycerin ester as the solvent for nitroglycerin and a propellant such as a flon gas into a gas pressurized container.

Conventional nitroglycerin sprays have defects such as a poor absorption of nitroglycerin thus sprayed, strong irritation of the oral mucosa and reduction in the amount of nitroglycerin sprayed each time with the reduction in the amount of the propellant in the sprayer after repeated spraying. Although these defects are quite disadvantageous for the medicinal preparations, they have not been overcome as yet.

SUMMARY OF THE INVENTION

After intensive investigations made for the purpose of developing a nitroglycerin spray free from the above-described defects, the inventors have found that when nitroglycerin is dissolved in a mixture of water with ethanol, the absorption of nitroglycerin through the oral mucosa is improved and the irritation is reduced because of the presence of water. The inventors have further found that when the pH of the solution is adjusted in the range of about 2.4 to about 6.7, preferably about 3.0 to about 6.5 and still preferably about 3.5 to about 6.0, the shelf stability thereof is increased and that by filling the solution into a liquid-pressurized, constant-feed container, a given amount of the solution can be sprayed constantly. The present invention has been completed on the basis of this finding.

The present invention relates to a spray prepared by filling an aqueous ethanol solution containing nitroglycerin and having a pH in the range of about 2.4 to about 6.7 into a liquid-pressurized container.

The aqueous ethanol solution of the present invention has a nitroglycerin content of about 0.05 to about 2 w/v %, preferably about 0.3 to about 1.2 w/v % and still preferably about 0.5 to about 1 w/v % based, on the whole aqueous ethanol solution.

The aqueous ethanol solution has an ethanol content of about 10 to about 85 v/v %, preferably about 30 to about 75 v/v % and still preferably about 50 to 70 v/v % based on the whole aqueous ethanol solution. The balance usually comprises water. The spray of the present invention is substantially free from any propellant such as a flon gas.

Since the stability of nitroglycerin in the aqueous ethanol solution varies depending on the pH, it is adjusted with a suitable acid or alkali, usually hydrochloric acid or sodium hydroxide.

Although the aqueous ethanol solution containing nitroglycerin to be filled into the liquid-pressurized container may contain corrigents such as sugars, amino acids and flavors, if necessary, the solution usually comprises only nitroglycerin, ethanol and the balance of water. The composition free of other components has a high stability and usually other components are unnecessary.

Although the amount of nitroglycerin sprayed each time varies depending on the concentration thereof in the aqueous ethanol solution, it is preferably about 0.3 to 0.4 mg. The amount of the aqueous ethanol solution sprayed each time is usually about 20 to 700 mg, preferably about 30 to about 400 mg.

The liquid-pressurized container is made of any of plastics, glass and aluminum. The plastics include, for example, high-density polyethylene, polyethylene terephthalate, polyvinyl chloride and polypropylene.

(Effect of the Invention)

The spray of the present invention gives a high nitroglycerin shelf stability, only a slight irritation of the oral mucosa and a high absorption of nitroglycerin thus sprayed as will be described in the following Examples.

(EXAMPLES)

(1) Experimental samples:

A liquid composition shown in Table 1 (prepared by a method described in Example 1 or a method similar thereto) was filled into a 10-ml liquid-pressurized, constant-feed polyethylene container designed so that about 40 mg of the solution can be sprayed each time. Sample No. 11 was a commercial product comprising a solution of nitroglycerin in a capric/caproic acid glycerin ester and a flon gas as the propellant filled into a gas-pressurized container.

(2) Evaluation method:

The experimental sample was stored in a thermostatic chamber at 50° C. to examine changes in the nitroglycerin content. Further, each sample was sprayed once in the oral cavity of each of 10 panel members to examine the irritation organoleptically. Each sample was sprayed once under the tongue of each beagle and the absorption of nitroglycerin was determined by measuring the concentration thereof in the blood.

(3) Results of experiment:

The results are shown in Table 1. The spray of the present invention exhibited no particularly strong irritation when it was sprayed into the oral cavity and was not unpalatable. The shelf stability of nitroglycerin was high. It could be absorbed through the sublingual mucosa. The spray thus satisfied the necessary conditions.

When the Spray No. 4 of the present invention and Comparative Spray No. 11 (gas-pressurized; dichlorodifluoromethane filled) were repeatedly sprayed 200 times, the amount of the liquid sprayed each time was invariably around 40 mg in the former, but was reduced a little (from around 50 mg to around 45 mg) as the gas pressure was reduced in the latter.

The following Examples will further illustrate the present invention, which by no means limit the invention.

TABLE 1

| Conditions | No. 1 Comp. Ex. | No. 2 Present invention | No. 3 Present invention | No. 4 Present invention | No. 5 Present invention | No. 6 Comp. Ex. | No. 7 Present invention | No. 8 Present invention | No. 9 Comp. Ex. | No. 10 Comp. Ex. | No. 11 Comp. Ex. |
|---|---|---|---|---|---|---|---|---|---|---|---|
| Sample | | | | | | | | | | | |
| Ethanol concentration v/v % | 60 | 60 | 60 | 60 | 60 | 60 | 5 | 80 | 90 | 100 | 0 neutral ester |
| pH | 2.4 | 3.0 | 3.5 | 5.5 | 6.5 | 7.0 | 5.6 | 5.7 | 5.6 | — | — |
| Amount of TNG sprayed each time (mg) | 0.3 | 0.3 | 0.3 | 0.3 | 0.3 | 0.3 | 0.3 | 0.3 | 0.3 | 0.3 | 0.4 |
| Amount of solution sprayed each time (mg) | 43 | 43 | 43 | 43 | 43 | 43 | 650 | 43 | 43 | 43 | 50 |
| 1. (Evaluation) Irritation upon spraying in the oral cavity substantially no irritation 0 slightly strong +1 strong +2 very strong +3 | +1 slightly hot | 0 sweet and slightly hot | 0 " | 0 | 0 " | 0 " | 0 solely sweet | 0 sweet and hot | +2 highly astringent | +3 highly astringent and pain caused in spray-contacting region | +1 slightly irritating |
| 2. Persistence of TNG (%) after storage at 64.2° C. for 14 days | 79.6 | 94.5 | 97.4 | 98.9 | 85.7 | 66.6 | 98.5 | 97.6 | 93.2 | 91.9 | 97.8 |
| 3. Bioavailability of TNG after sublingual administration to beagles | | | | | | | | | | | |
| 1 Maximum blood concentration (ng/ml) | | | | 8.9 | | | 8.7 | | | 8.1 | 2.6 |
| 2 Area under the blood concentration-time curve (ng · min/ml) | | | | 45.9 | | | 44.6 | | | 43.7 | 32.3 |

EXAMPLE 1

Nitroglycerin was dissolved in a 60 v/v % aqueous ethanol solution to give a solution having a concentration of 0.75 w/v %. The pH of the solution was adjusted to 5.5 with 0.01 N hydrochloric acid. 10 m( of the solution was filled into a polyethylene bottle having a liquid-pressurized spray nozzle which was so designed that 43 mg of the solution could be sprayed each time. The bottle was hermetically sealed to give a spray which can spray about 0.3 mg of nitroglycerin into the oral cavity each time.

EXAMPLE 2

Nitroglycerin was dissolved in a 5 v/v % aqueous ethanol solution to give a solution having a concentration of 0.046 w/v %. The pH of the solution was adjusted to 5.0 with 0.01 N hydrochloric acid. 20 ml of the solution was filled into a polypropylene bottle having a liquid-pressurized spray nozzle which was so designed that 650 mg of the solution could be sprayed each time. The bottle was hermetically sealed to give a spray which can spray about 0.3 mg of nitroglycerin into the oral cavity each time.

EXAMPLE 3

A spray having an ethanol concentration of 80 v/v % and a pH of 5.7 was prepared in the same manner as that of Example 1.

We claim:

1. A nitroglycerin spray prepared by filling a solution having a pH of about 3.0 to about 6.0 and consisting essentially of the following components (a), (b) and (c) and substantially free from other components:
    (a) about 0.5 to about 1 w/v %, based on the whole solution, of nitroglycerin,
    (b) about 50 to about 70 v/v %, based on the whole solution, of ethanol, and
    (c) the balance of water, into a container.

2. In the art of spraying compositions containing nitroglycerin into the oral mucosa, that method of improving absorption of nitroglycerin through the oral mucosa and reducing irritation which consists essentially of the step of administering the nitroglycerin spray defined by claim 1.

* * * * *